United States Patent [19]

Pelyva et al.

[11] Patent Number: 4,931,585
[45] Date of Patent: Jun. 5, 1990

[54] PROCESS FOR PREPARING N-PHOSPHONO-METHYL-IMINO-DIACETIC ACID

[75] Inventors: Jenó Pelyva, Füzfőgyártelep; Csaba Söptei, Veszprém; Zoltán Kolonics, Balatonalmádi; Béla Karácsonyi, Budapest; Sándor Bálint; Jánosné Benczik, both of Balatonalmádi; Csaba Kayos, Veszprém; László Lendvai; Sándor László, both of Füzfőgyártelep, all of Hungary

[73] Assignee: Nitrokémia Ipartelepek, Fuzfögyártelep, Hungary

[21] Appl. No.: 306,032

[22] Filed: Feb. 2, 1989

[30] Foreign Application Priority Data

Feb. 8, 1988 [HU] Hungary .................. 2251-562/88

[51] Int. Cl.$^5$ ............................................... C07F 9/38
[52] U.S. Cl. ..................................... 562/17; 562/554; 562/571
[58] Field of Search ................... 260/502.5 F; 562/17

[56] References Cited

FOREIGN PATENT DOCUMENTS 2154589  9/1985  United Kingdom ............... 562/11

OTHER PUBLICATIONS

Chem. Abstracts, vol. 95, 20331t, 1981.

*Primary Examiner*—J. E. Evans
*Attorney, Agent, or Firm*—Schweitzer & Cornman

[57] ABSTRACT

The invention relates to the preparation of N-phosphono-methyl-imino-diacetic acid from the calcium salt of imino-diacetic acid in a simplified synthesis. The process comprises in that the imino-diacetic acid calcium salt is heated with concentrated hydrochloric acid in a molar ratio of 2-3:1 at a temperature between 50°–100° C., the obtained imino-diacetic acid hydrogenchloride is separated then dissolved in water and is reacted with phosphorous acid in a molar ratio of 1.0-1.2:1 calculated for imino-diacetic acid hydrogen chloride and with the aqueous solution of formaldehyde in a molar ratio of 1.0-1.4:1 under stirring, and the obtained product is isolated.

3 Claims, No Drawings

PROCESS FOR PREPARING N-PHOSPHONO-METHYL-IMINO-DIACETIC ACID

The invention relates to the preparation of N-phosphono-methyl-imino-diacetic acid starting from the acidic calcium salt of imino-acetic acid.

N-phosphono-methyl-imino-diacetic acid is an important intermediate during the preparation of N-phosphono-methyl-glycine (glyphosate) of wide activity spectrum. HU-PS No. 177,155 relates to the preparation of N-phosphono-methyl-imino-diacetic acid, wherein the acidic calcium salt of imino-diacetic acid is described. According to this patent specification the double salt of formula A

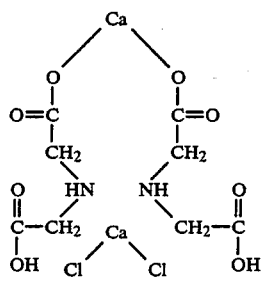

is prepared by adding calcium-hydroxide to the ammonium salt of monochloro-acetic acid in aqueous medium in a given molar ratio removing ammonia from beside the soluble imino-diacetic acid calcium salt, and adjusting the pH-value of the solution with hydrochloric acid to a value between 2 to 6. Purpose of the preparation of the double salt is to prepare N-phosphono-methyl-imino-diacetic acid during which the aqueous suspension of the double salt is subjected to double decomposition with a sodiumsulphate solution in a molar excess of 30%, the gypsum formed is centrifuged and the aqueous solution of imino-diacetic acid monosodium salt is reacted with paraformaldehyde in a molar excess of 50% and with phosphorus-trichloride in a molar excess of 5%. After the reaction aqueous sodium-hydroxide solution is added and the product is separated by cooling. Yield is about 60% calculated for monochloric acetic acid. Disadvantage of the described process is that by adding sodium salt used to double decomposition the amount of the inorganic salt forming in the process and polluting the environment strongly increases. From the great amount of phosphorus trichlorid used by reacting double calcium salt hydrochloric acid is formed, which should be neutralized by using sodiumhydroxide in order to achieve the precipitation of N-phosphono-methyl-imino-diacetic acid with suitable yield. By adding sodium hydroxide a further amount of sodium-chloride is formed in the process, which pollutes the end-product. Because of the use of phosphorus-trichloride the binding of the significant amount of hydrochlorid acid requires considerable costs.

Subject of the invention is to prepare N-phosphono-methyl-imino-diacetic acid on one side by simplified synthesis, on the other side for eliminating the formation of side products polluting the environment.

The process according to the invention for preparing N-phosphono-methyl-imino-diacetic acid by using the imino-diacetic acid calcium salt formed from monochloric acetic acid, ammonia and calcium-hydroxide can be characterized by heating the calcium salt of imino-diacetic acid with concentrated hydrochlorid acid in a molar ratio of 2-3:1 at a temperature between 50°-100° C., separating the obtained imino-diacetic acid hydrochloride, then dissolving it in water and optionally after purification reacting it with phosphorous acid in a molar ratio of 1.0-1.2:1 and with the aqueous solution of formaldehyde in a molar ratio of 1.0-1.4:1 under boiling, isolating the obtained product optionally after evaporating the mixture.

The process according to the invention is carried out as follows:

Into the aqueous solution of 60% monochloracetic acid ammonia is added at 20°-30° C. in a molar ratio of 0.6:1. After the addition is finished calcium-hydroxide is added to the reaction mixture in small doses at 35°-40° C. in a molar ratio of 1.05:1 under cooling. The imino-diacetic acid calcium salt formed during the reaction is transformed into imino-diacetic acid hydrochloride by using concentrated hydrochloric acid in a molar ratio of 2.5:1 by boiling the mixture at 60°-80° C. After the reaction the mixture is cooled to 10°-20° C. the precipitated imino-diacetic acid hydrochloride is filtered, then after transformation into imino-diacetic acid it is dissolved in water, the mechanical impurities are removed and phosphorous acid is added in a molar ratio of 1.05:1. The mixture obtained is heated to its boiling point and formaldehyde is added in a molar ratio of 1.2:1 in the form of aqueous solution. The N-phosphonomethyl-imino-di-acetic acid obtained is filtered.

Advantages of the process according to the invention can be summarized as follows:

the end-product can be prepared with good yield in a simplified synthesis, isolating of imino-diacetic acid is not necessary, the process can be carried out in less steps and much less side-product are formed, for neither the preparation of imino-diacetic acid from its hydrochloride, nor the transformation of the calcium salt of imino-diacetic acid into sodium salt are necessary, the imino-diacetic acid hydrochloride intermediate can directly be used as the starting material of the process according to the invention without purification and drying, the technical difficulties, such as the neutralization of the great amount of hydrochloric acid formed during preparation can be eliminated by using phosphorous acid, the process can be carried out in simple apparatuses-/equipments.

The process according to the invention is described in detail in the following non-limiting Examples.

EXAMPLE 1

Into a coolable, heatable, enamelled autoclave with a volume of 500 liter equipped with a stirrer, thermometer, and reflux condenser 190 kg of 50% aqueous monochloro-acetic acid solution (1.0 kmole) was introduced. After cooling 12.75 kg (0.75 kmole) of ammonia gas was introduced into the solution under stirring. While keeping the temperature of the reaction mixture at 35°-40° C., 77.7 kg (1.05 kmole) of calcium-hydroxide was added in equal doses within 1.5-2.5 hours. The reaction mixture obtained is then stirred for 6 hours at a temperature between 40°-50° C. 50 liter of this mixture was then distilled off in vacuo at a temperature around 80° C. for removing the ammonia excess. 200 liter of 37% hydrochloric acid was then added to the reactor and it was stirred for one hour at 60°–80° C. The reaction mixture obtained was cooled to 10°–20° C. and after stirring for 2–3 hours the imino-diacetic acid hydrogen chloride was filtered out.

Imino-diacetic acid-hydrogen chloride was obtained in an amount of 101 kg, containing 30% humidity. Thereafter it was solved in 100 liter of water, filtered from the mechanical impurities, then analyzed. The aqueous solution contains about 68 kg of imino-diacetic acid-hydrochloride, which is 80% of the theoretical amount.

The aqueous solution was then heated with 34.1 kg (0.4 kmole) of 96% phosphorous acid in an autoclave equipped with heatable-coolable cooler and reflux condenser and stirrer at the temperature of the boiling point of the mixture. 39.7 kg (0.45 kmole) of a 34% aqueous formaldehyde solution was added within an hour then stirred for further 2 hours at boiling point. Thereafter it was cooled to 10°–15° C. and the precipitated N-phosphono-methyl-imino-diacetic acid was filtered out, washed with water then dried. 78,6 kg of product are obtained which is of 98.2%. Yield of the phosphonomethylating step is 85.1%, the yield calculated for monochlor-acetic acid is 67.9%.

EXAMPLE 2

Into an enamelled apparatus of a volume of 500 liter equipped with coolable-heatable stirrer, cooler and refluxing cooler 154.5 kg (1.0 kmole) of 60% aqueous monochlor-acetic acid solution was introduced. 11.1 kg (0.65 kmole) of ammonia gas was introduced into the apparatus under cooling and stirring. The temperature of the reaction mixture was kept at 35°–40° C. and 77.7 kg (0,05 kmole) of calcium-hydroxide are added in equal parts within 2 hours. The reaction mixture obtained was stirred at 45°–50° C. for 7 hours, 200 liter of a 37% aqueous hydrochloric acid solution was added, then stirred for an hour at 60°–80° C. The reaction mixture obtained was cooled to 10°–20° C., crystallized for 3–4 hours then filtered. 105 kg of solid product was obtained with 30% humidity.

This product was dissolved in 100 liter of water, the mechanical impurities were filtered out and introduced into an autoclave equipped with a coolable-heatable cooler and reflux condenser and stirrer. On the basis of analysis imino-diacetic acid-hydrogenchloride amount in the solution obtained was 69.7 kg (0.41 kmole). 19.7 kg (0.2 kmole) of a 37% hydrochloric acid and 40.3 kg (0,49 kmole) of phosphorous acid were added to the solution. The reaction mixture obtained was heated to its boiling point and at the temperature of the boiling point 43.4 kg (0,49 kmole) of 34% aqueous formaldehyde solution was added within an hour then the reaction mixture was boiled for further 2 hours. It was then evaporated to ⅔ of its original volume, cooled to 10°–15° C., the precipitated crystals were filtered, washed with water and dried. 79.4 kg of N-phosphono-methyl-imino-diacetic acid was obtained with a purity of 98%, which decomposes at 208°–209°. Yield of the phosphonomethylating step is 83.6%, yield calculated to monochloracetic acid is 68.0%.

We claim:
1. A process for preparing N-phosphonomethyl-imino-diacetic acid which comprises the steps of
   (a) forming an imino-diacetic acid calcium salt by reacting monochlor-acetic acid, ammonia and calcium hydroxide;
   (b) heating the calcium salt of imino-diacetic acid with concentrated hydrochloric acid in a molar ratio of from 2–3 to 1 at a temperature between 50° and 100° C. to form imino-diacetic acid HCl;
   (c) recovering by filtration the imino-diacetic acid HCl;
   (d) dissolving the recovered imino-diacetic acid HCl in water to form a solution;
   (e) reacting the solution while stirring, by heating it with phosphorous acid in a molar ratio of from 1.0–1.2:1, based on the imino-diacetic acid HCl and with an aqueous solution of formaldehyde in a molar ratio of from 1.0–1.4:1;
   (f) cooling the reaction mixture to precipitate the N-phosphonomethyl-imino-diacetic acid, and
   (g) filtering the precipitated N-phosphonomethyl-imino-diacetic acid.

2. The process of claim 1, wherein in said step (d), after dissolving the imino-diacetic acid HCl in water, the solution is filtered and the filtrate is further reacted.

3. The process of claim 1, wherein after step (e), the reaction mixture is evaporated to reduce the volume and then cooled to precipitate the N-phosphonomethyl-imino-diacetic acid.

* * * * *